(12) United States Patent
Cartledge et al.

(10) Patent No.: US 6,227,861 B1
(45) Date of Patent: May 8, 2001

(54) PREFORMED MANDIBULAR SPLINT

(76) Inventors: Richard G. Cartledge; John P. Cartledge, both of 4271 Mangrum Ct., Hollywood, FL (US) 33021

( * ) Notice: Subject to any disclaimer, the term of this patent is extended or adjusted under 35 U.S.C. 154(b) by 0 days.

(21) Appl. No.: 09/514,990

(22) Filed: Feb. 29, 2000

(51) Int. Cl.$^7$ ................................. A61C 5/00; A61C 3/00
(52) U.S. Cl. ................................................ 433/215; 433/18
(58) Field of Search .................... 433/18, 19, 24, 433/215, 37, 38, 47, 6

(56) References Cited

U.S. PATENT DOCUMENTS

| | | | |
|---|---|---|---|
| 2,634,500 | * | 4/1953 | McAdoo .................................. 433/38 |
| 3,487,545 | * | 1/1970 | Weissman ............................ 433/215 |
| 4,202,328 | * | 5/1980 | Sukkarie ................................ 433/18 |
| 4,230,104 | * | 10/1980 | Richter .............................. 433/19 X |
| 4,433,960 | * | 2/1984 | Garito et al. ........................ 433/215 |
| 4,735,571 | * | 4/1988 | Salvo .................................... 433/215 |
| 5,842,856 | * | 12/1998 | Casey ................................... 433/19 |
| 6,086,365 | * | 7/2000 | Fields ............................... 433/215 X |

* cited by examiner

Primary Examiner—Nicholas D. Lucchesi
(74) Attorney, Agent, or Firm—Herbert M. Hanegan, Esq.

(57) ABSTRACT

A preformed mandible splint and a method of aligning and stabilizing a fractured mandible with such a splint is disclosed. The splint is configured to approximate the curvature of the lower teeth or the gingiva of the lower jaw. The curvature of an eight inch diameter sphere approaches the geometric curvature of the human teeth and gum, therefore, the similarly configured splint of the present invention is usable for almost any child or adult. The splint is approximately U-shaped, follows the human dental arcade, and has rows of holes or slots along its outer and inner perimeter. The splint is placed on the teeth or gingiva and wired through the holes or slots to the mandible thus correctly aligning the mandible. Fractures can then be screwed into place according to the curvature of the splint. This eliminates the need of wiring the patient's jaw shut as is presently done in current interdigitation techniques where even minute errors in mandibular repair results in flagrant morbidities in the patient. The U-shape allows the patient's tongue to freely move. Because the splint uniformly fits the population it can be preformed. The gumline follows the same curvature as the teeth, therefore the splint may be used on those without teeth by being placed directly on the gingiva.

25 Claims, 3 Drawing Sheets

PREFORMED MANDIBULAR SPLINT

FIELD OF THE INVENTION

This invention relates to a dental appliance, and more particularly to a mandibular splint and method for alignment and stabilization of a fractured mandible.

DESCRIPTION OF THE PRIOR ART

Mandibular fractures have historically been one of the most difficult procedures for the reconstructive surgeon. The slightest damage to this complex structure causes disruption of the relationship between 32 teeth and 2 joints. The most minute operative error during mandibular repair will result in flagrant post-operative morbidities including headaches, TMJ arthralgias, chronic ear and jaw pain, sleepless nights, and anorexia. The principle used by reconstructive surgeons for proper mandibular reduction and repair is based upon the assumption that interdigitation of the maxillary and mandibular arches of teeth will serve to properly align the mandible in it's single, correct position. The mandible is fixed in this position using mandibulomaxillary fixation (MMF). The patient is left in MMF for an average of 6 weeks. This method of correcting mandibular fractures has long been the standard procedure despite it's many shortcomings.

Proper reduction and fixation is possible when the patient has an intact mandibular and maxillary arch of teeth. The patient's teeth serve as an accurate template; they interlock in only one proper position which is consistent and reproducible. However, when the patient does not have ideal dentition due to oral trauma, has prior dental extractions, or an edentulous arch, the surgeon must attempt to estimate the mandibular reduction using direct visualization and TMJ positioning alone. There exists no device in the prior art to aid the surgeon in reapproximation of the mandible.

In the patient whose mandible is fractured, it is extremely important that the mandible is properly aligned and stabilized for repair. Incorrect alignment can lead to morbidity and malocclusion. Repair of a fractured mandible involves two steps: realignient of the dislocated fragments and stabilization of the bone. The current technique for correcting mandibular fractures is to provide alignment and stabilization by interdigitation of the teeth. Prior art methods of mandibular fracture repair use interdigitation accomplished by wiring the mouth closed so that the mandible interacts with the maxilla to align and stabilize the mandible. After fracture stabilization, the patient's mouth is left wired shut for a period of six weeks.

This technique, however, has many drawbacks. In order to prepare the patient's mandible for fixation, the surgeon must first begin the long and arduous task of affixing arch bars to the teeth. This process alone takes several hours while the patient is under general anesthesia. Since the surgeon is relying on the patient's teeth as a template, those who are edentulous, or have damaged or missing teeth (which is commonly the case due to the inciting traumatic event) are unlikely to be aligned properly. Furthermore, there are serious problems with long-term fixation of the mandible to the maxilla such as discomfort of the patient, problems clearing oral and respiratory secretions which can lead to airway blockage, increased incidence of dental carries, weight loss, malnutrition, and increased risk of gingival infections and osteomyolitis of the mandible and maxilla. The most significant of the aforementioned complications is airway compromise. There have been a number of reported cases of patients who have died after mandibular wiring because they were unable to clear respiratory secretions or vomitus from their airway. Other deaths have been reported due to postoperative oropharyngeal swelling because of the patients' inability to open their mouths to breath adequately. Thus, there is a need for an accurate method of aligning and stabilizing a fractured mandible without requiring the interdigitation of teeth and the wiring shut of the mouth.

Various splints have been designed for dental use. Splint designs have been reviewed by Clark, Journal of the American Dental Association, 108:359–363 (1984); and Clark, Journal of the American Dental Association, 108:364–368 (1984). Methods of fabricating occlusal splints have also been described by Wright, Journal of the American Dental Association, 117:757–758 (1988). These splints typically cover the teeth of the lower dental arch and interdigitate with the teeth of the opposing upper arch. Such splints are manufactured by an indirect process in which the dentist takes an impression of the patient's teeth and makes a registration of the jaws in the desired therapeutic position. A splint is then indirectly manufactured in a laboratory from the impression and registration obtained by the dentist. The fabricated splint is typically returned to the dentist after a significant period of delay, and the splint is then placed in the patient's mouth. For instance, Summer U.S. Pat. No. 5,173,048 discloses a dental splint that covers the teeth of a lower dental arch and interdigitates with the teeth of a second dental arch to change the bite surface. These splints, however, are not useable for mandibular fractures, but only for other dental problems such as temporomandibular joint (TMJ) disorder. In addition, these splints require taking impressions of the teeth and thus are not quickly available, and are expensive due to the custom fitting that must be performed. Such splints must also rely on interdigitation of the teeth which is not of use in the edentulous patient. There are several significant disadvantages with this indirect fabrication technique. One serious drawback is that indirect fabrication usually requires at least several days to complete because the dentist must send the impression and registration to an outside laboratory. Unfortunately, patients with an injury are often in serious pain and need a splint immediately, particularly after a traumatic joint injury. Any period of delay in placing the finished splint in the patient's mouth can cause unbearable pain during the period of delay.

A further disadvantage with indirect fabrication methods is that they increase the cost of the dental splint. Making impressions and sending them to a laboratory for conversion into a splint is costly. It multiplies the fabrication steps and increases the number of parties involved in the manufacturing chain. The expense associated with these multiple steps sometimes makes the splint more expensive than a patient can afford or an insurer is willing to pay.

Another disadvantage with indirect fabrication is that it is inaccurate because the existing anatomy has been fractured and the mold is therefore of a configuration which is not correct. Bite registration must be very precise to be acceptable and helpful to patients. Unfortunately, a therapeutic bite constructed indirectly in the laboratory seldom fits perfectly in the patient's mouth. The indirectly fabricated splint must be adjusted by the dentist with the patient present. Such adjustments further increase the manufacturing expense and often result in a bite surface which is still not entirely accurate.

Thus, there is a need for a dental splint which may be used for the repair of mandibular fractures, that does not require an impression and can be used on a wide variety of patients, does not require interdigitation of the teeth, and is sufficiently uniform to be readily available in an emergency.

Other prior art methods of fixation consist of a splint of a shape to correspond with the lower jaw, and sufficiently rigid to keep the parts of the fractured bone in place and a head piece formed to fit the top of the head, and serve as a support to the splint; the two parts being connected together by straps, so that the splint will be held in place by the head piece.

Other fracture appliances and bandages for fractures of the maxillary bones have sleeves, a chin cup, means adjustably securing said cup to the sleeves, a head piece extending over the head means securing said sleeves to said head piece at a point corresponding with the junction of the condyles of mandible with the glenoid fossa, to allow horizontal motion to conform to the opening and closing of the mouth.

Still other methods relate to splints for the immobilization of the mandible and have a one-piece harness having a chin support on one portion thereof and an occiput engaging support on another portion thereof. The supporting harness fits over the head and engages the chin and the occiput and is curved along the side of the head over the ears. A strap passes over the top of the head for attaching the two curved portions passing over the ears together and are connected so as to pull the patient's chin anteriosuperiorly and bring the teeth into occlusion. A pair of posterior straps connect the occiput engaging support portion with the chin support portion of the supporting harness by means of connections.

Current methods of interdental immobilization entail the use of arch bars, i.e. a pliable metal strip with projecting hooks known as an arch bar and several fine wires and rubber bands. The metal strip is secured tightly to the teeth of the upper jaw by passing a wire around the base of a tooth, through the gum and over each side of the tooth and over the metal strip. At this point, both ends of the wire are outside the mouth and are twisted together to hold the metal strip urgingly against the outside surface of the teeth. The twisted wire is then cut and bent backward towards the gum and preferably placed in between two adjacent teeth to prevent irritation on the inside of the lips.

This is repeated spatially around eight to twelve teeth of the upper jaw and the same is repeated over the lower jaw.

The metal strip has the projecting hooks spatially disposed on its outside surface and over these hooks. Rubber bands or wires are then attached between those hooks of the metal strip attached to the teeth of the lower jaw and those hooks of the upper jaw.

This particular prior art technique has several disadvantages. The most dominant disadvantage is that during twist tightening of the wires, the wires can easily snap and the whole process must be repeated hence adding to the length of the installation procedure. It is not uncommon for this procedure to take between two to four hours of operating theatre time since a general anesthetic for the this part of the procedure is always needed.

After approximately two days of use, the wires need to be retightened and retwisted as they have a tendency to loosen off and sometimes break. If they break during tightening, the patient must be re-anesthetized again within the operating theatre and new wires inserted as before. Further, the patient must be anesthetized for wire removal after the jaw has mended. Another prior art method for fixing the mandible of a patient to allow fractures therein to heal comprises positioning an arch bar on a first set of teeth; inserting a cable tie in the space between first and second adjacent teeth and between said second tooth and a third tooth such that the cable tie overlies a portion of said arch bar; locking the cable tie to secure the arch bar to said second tooth; providing a plurality of additional cable ties to secure said arch bar to other teeth in said first set of teeth; positioning an arch bar on a second set of teeth adjacent said first set of teeth and secured thereto by a cable tie, each arch bar having a plurality of hook members formed therein; and engaging adjacent hook members on each arch bar with a resilient member to fix the mandible.

Accordingly it is an object of the present invention to provide a method for rapidly, efficiently and accurately aligning and stabilizing a fractured mandible which does not require wiring the mouth shut.

Another object of this invention is to provide long-term stabilization of the mandible for the full duration of the healing period of the fractures.

Another object of this invention to provide a mandibular splint which does not require interdigitation of the teeth and may be used on the edentulous patient, or those with damaged or incomplete dentition.

A further object of the present invention to provide a mandibular splint that can be prefabricated without requiring an impression of the patient's teeth.

Another object of this invention to provide a uniform mandibular splint which can be used on a wide variety of patients.

Another object of this invention is to substantially reduce the operative time it takes to perform the procedure, thus reducing cost and morbidities associated with prolonged general anesthesia times.

SUMMARY OF THE INVENTION

The present invention provides a mandibular splint and a method for using the mandibular splint which overcomes the deficiencies of the prior art. This invention is usable by almost any child or adult since the geometry of the human mandibular structure is highly uniform. The present invention comprises a splint manufactured to conform to a formula defining the general geometric structure of the human mandible. Advantageously, the present invention is a dental appliance for aligning and stabilizing the mandible for the correction of mandibular fractures comprising a splint having a curvature shaped to substantially conform in three dimensions to the curvature of the lower teeth or the gingiva of the lower jaw. Preferably, the splint conforms to Monson's Curve, i.e. the curvature of an 8 inch diameter sphere, which curvature follows the curvature of the human teeth and gumline. Accordingly, a splint can be preformed in accordance with such curvature and provide a means of aligning and stabilizing the mandible. The splint is placed on the teeth of the lower jaw or the gingiva and then fixedly wired to the mandible. As the splint is secured to the mandible, the fractures are reduced, and mandibular fragments approximated. The surgeon is now able to fixate the bony mandible in it's proper position with plates and screws or through external fixation.

A patient with a mandibular fracture will have the splint wired to the mandible after lying it over the teeth. Since the gumline follows the same geometric formula, an edentulous patient would have the splint wired directly against the gumline. During fixation of the splint, any fractures will naturally be returned to their proper positions. In such case the mandible will then have plates and screws secured across each fracture to allow for definitive fixation of the fractures in their proper positions.

Advantages of the present invention include: the more rapid, efficient, and accurate reduction and fixation of the fractures, the ability to easily manipulate any bony fragment that remains out of place after the splint is attached to the mandible, and importantly, there is no need for wiring the jaw shut, thus reducing the mortality and morbidity associated with this procedure.

DETAILED DESCRIPTION OF THE PREFERRED EMBODIMENTS

Figure 1:
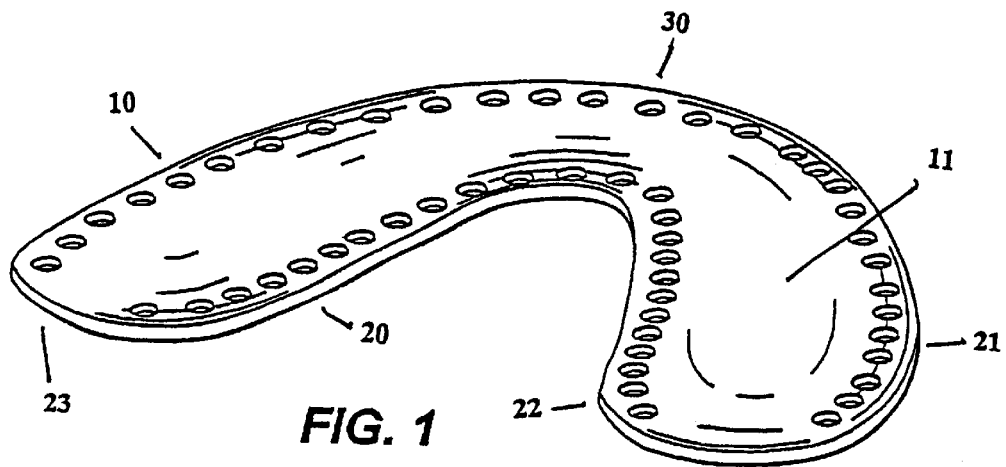
FIG. 1 is a perspective view showing the mandibular splint.
Figure 2:
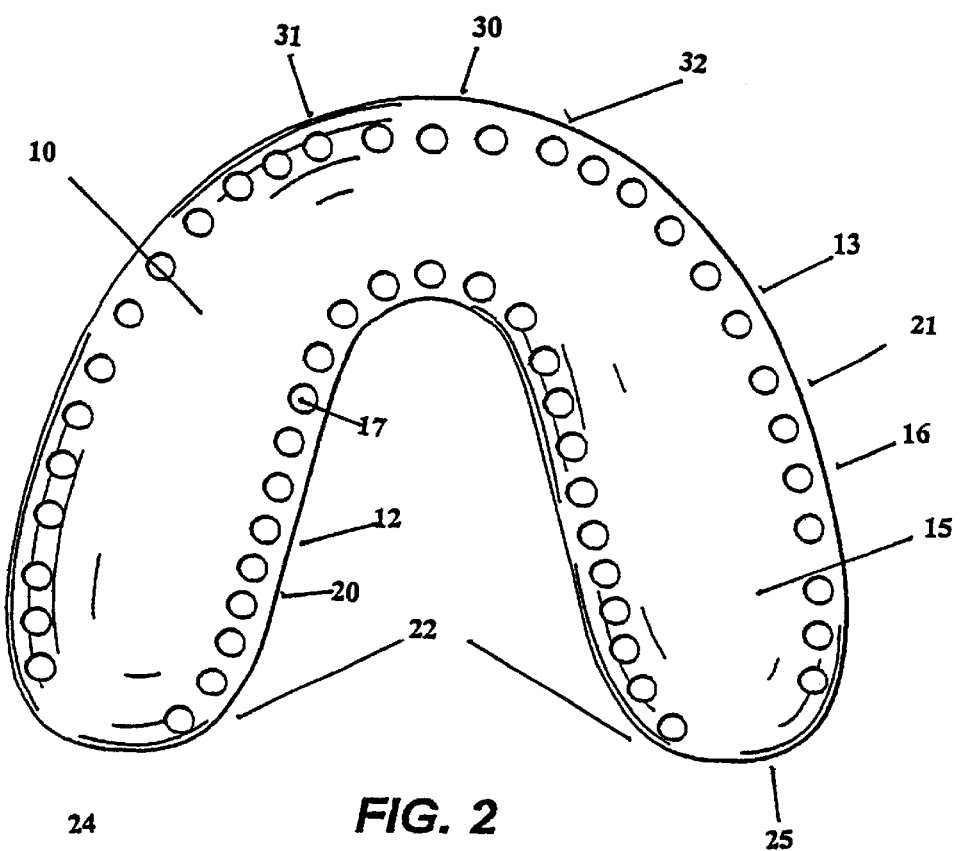
FIG. 2 is a front elevation view showing the mandibular splint.

In one embodiment the splint of the present invention consists generally of a modified U-shaped appliance as shown in FIGS. 1 and 2; i.e. the two legs of the U are not parallel, but become somewhat further apart as they approach the top of the U than they are at the bottom portion of the U. The splint 10 preferably has a generally U-shaped body 11 which generally follows the dental arcade. The splint has an inner U-shaped border 12 corresponding to the tongue or lingual side 20 of the splint and an outer U-shaped border 13 corresponding to the cheek or buccal side 21 of the appliance. The U-shaped configuration allows the patient to move the tongue, swallow, and breath adequately when the splint is inserted into the patient's mouth. The surface between the inner border 12 and outer border 13 defines a bite surface 15. The body has a front 30 at the base of the U-shape and a rear 22. The rear further having ends 23. The splint body has a first end 24 and a second end 25 The width of the bite surface gradually increases as it extends from the front 30 to the rear 22 and the ends 23 are tapered to avoid sharp edges. The splint also has a front first side 31 and a second side 32 symmetrical about a centerline.

Figure 3:
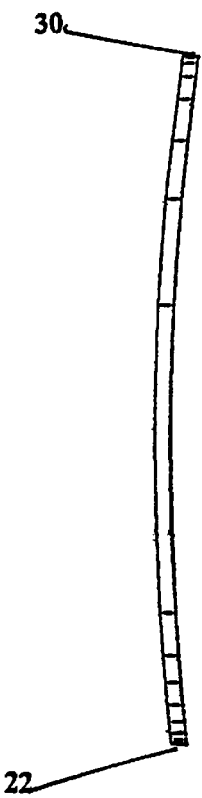
FIG. 3 is a side elevation view showing the mandibular splint and its curvature from front to rear.
Figure 4:
FIG. 4 is a rear plan view showing the mandibular splint and its curvature from side to side.
Figure 5:
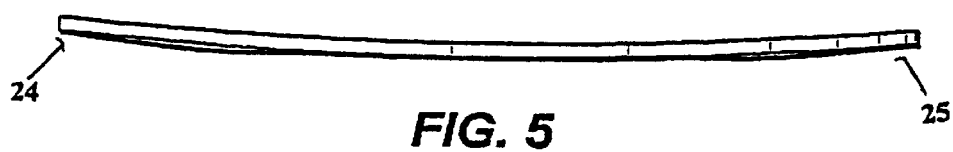
FIG. 5 is a front plan view showing the mandibular splint and its curvature from side to side.

Advantageously the present invention is a dental appliance for aligning and stabilizing the mandible for the correction of mandibular fractures comprising a splint having a curvature shaped to substantially conform in three dimensions to the curvature of the lower teeth or the gingiva of the lower jaw. Preferably, the splint is curved in three dimensions to substantially conform to Monson's Curve, i.e. in accordance with the curvature of an eight inch diameter sphere. This is a curvature corresponding to the geometric shape of the human teeth and gumline, i.e. the splint is curved from front to back in correspondence to the curvature of an eight inch diameter sphere. The front to back curvature is shown in FIG. 3. The body is also curved from side to side corresponding to the curvature of an eight inch diameter sphere. The side to side curvature can be seen in FIGS. 4 and 5. The splint of the present invention advantageously may substantially conform to the three dimensional curvature consistent with the Curve of Spee or with the Curve of Wilson.

The thickness of the splint should be sufficient to provide sufficient rigidity yet thin enough not to be uncomfortable when inserted in the patent's mouth. Advantageously, the splint is from about 0.2 to about 4.0 mm thick, preferably the splint is approximately 1 mm thick. Advantageously the splint is made of metals, metal alloys, plastics, ceramics, composite, and mixtures thereof In a preferred embodiment, the splint is made of methlymethacrylate or a metal alloy.

The bite surface should be of sufficient width to fit over the teeth (or the gingiva in the edentulous patient) and allow sufficient room for through holes (or slots) for wiring the splint to the mandible. For a standard adult a width of from about 18 to about 28 mm is sufficient. It should be noted that although the curvature of the splint is the same for all patients—that of an eight inch diameter sphere—the size of the mouth of the patient may differ. Thus, the size width of the bite surface may be smaller or different if the splint is to be used for a child as opposed to an adult.

In one embodiment the splint has an outer row of through holes 16 running along the bite width near the outer border 13 and an inner row of through holes 17 running along the bite width near the inner border 12. The through holes are sufficiently large in diameter to allow for the insertion of surgical wire, advantageously having a diameter of from about 0.25 mm to about 2.5 mm, preferably about 1.5 mm in diameter. The number of through holes may vary but should be enough to flimly afix the splint to the mandible. Because the outer boarder 13 is longer than the inner boarder 12 the number of holes 16 in the outer boarder may be more numerous than the holes 17 of the inner border. In such case one or more holes 16 may either not be used, or the wire from more than one hole 16 may be inserted through a hole 17. Advantageously the splint may have inner and outer slots instead of holes for fixing the splint to the mandible. Alternatively the splint may be indirectly attached to the mandible by affixing it to arch bars secured to the teeth or by affixing it to brackets secured to the mandible.

Figure 6:
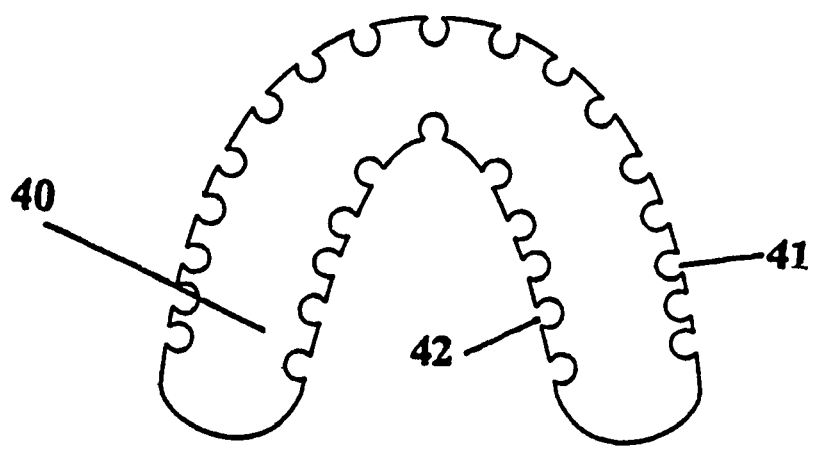
FIG. 6 is a front elevation view showing an alternate embodiment of the present invention.
Figure 7:
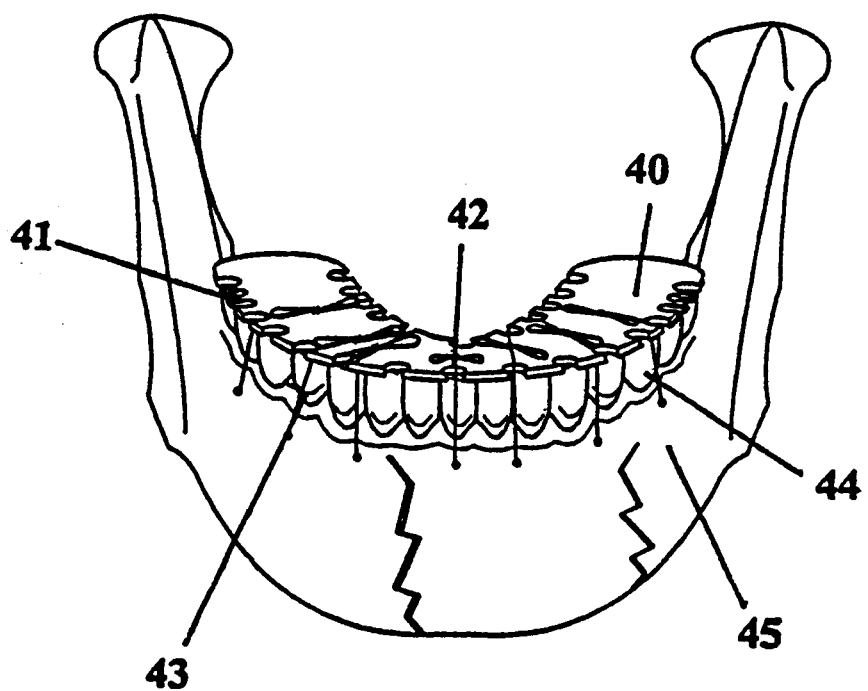
FIG. 7 is a front view showing the embodiment of FIG. 6 attached to the mandible.

In an alternative embodiment, as shown in FIGS. 6 and 7, splint 40 may have slots or indentions 41, 42 instead of holes 16, 17 (shown in FIG. 2). Regardless of the embodiment used, the splint is placed over teeth 44 and attached to mandible 45 by a connection means 43, preferably a surgical type wire.

To provide alignment and stabilization of the teeth, the splint is placed on the teeth (or the gingiva in the edentulous patient) of the lower jaw. The splint is then fixed to the lower jaw by wiring to the mandible using the through holes 16 and 17. The fixation of the splint to the teeth aligns the mandible and provides stabilization thereby reducing the fractures to their proper positions. Mandibular fragments are then put in place in accordance with the alignment provided by the splint such as by using plates and/or screws across each fracture. This technique also avoids the difficulties involved with wiring the mouth shut, such as difficulty in manipulating bony fragments into place.

EXAMPLE

A methlymethacrylate plate was constructed conforming exactly to the three-dimensional contour of an eight-inch radius sphere. One hundred articulated plaster dental casts of 50 male and 50 female adult patients were randomly selected by a dental technician. The patients from which the plaster casts were obtained varied in dentitional state from having completely intact upper and lower arches of teeth, to patients with numerous extractions, to the completely edentulous patient. Blue colored bite paper was used in order to define the original occlusion of the articulated models (bite paper leaves an ink mark on the teeth at their points of contact). The mandibular components of all plaster casts were then removed from the articulators. The mandibular casts were struck with a rubber mallet yielding simulated fractures ranging from single symphyseal to complex, combined symphyseal/para symphyseal fractures. The fractured edges were ground smooth with sandpaper to ensure that reapproximation would be attributable solely to the present inventive splint.

The broken segments of each cast were reapproximated by using a splint of the present invention as a universal template. The segments were then fixated with plates and screws. The newly reconstructed mandibular models were then reapplied to their respective articulators. Yellow colored bite paper was then used to demarcate the occlusal surfaces of the reapproximated mandibular casts. The accuracy of the reapproximation of the mandibular casts utilizing the present splint was assessed by comparing the bite paper markings from the original casts to the repaired casts.

RESULTS:

Overlapping blue and yellow markings left on the plaster teeth produced a green spot at each point that corresponded between the ongmal and repaired casts. Therefore, if a cast contained only green markings, it was assumed that the fracture repair had restored the original occlusion to exacting proportions and was considered a success. Any cast which displayed yellow or blue bite-paper ma-idngs was considered malocclusion and a failure. Of the 100 fractured mandibular casts reapproximated and repaired using the present inventive splint, 98 were successes. Two reapproximations were failures.

Having illustrated and described the principles of the invention in several preferred embodiments, it should be apparent to those skilled in the art that the invention can be modified in arrangement and detail without departing from such principles.

What is claimed is:

1. A dental appliance for aligning and stabilizing the mandible for the correction of mandibular fractures comprising a splint having a curvature which substantially conforms to the three dimensional curvature of an 8-inch diameter sphere, having an inner border and an outer border, and attachable directly or indirectly to the mandible.

2. The appliance of claim 1 having a curvature which substantially conforms to the natural occlusal curvature.

3. The dental appliance of claim 1 wherein said splint has a modified U shape with the two legs of the U not being parallel, but being further apart at the top of the U than at the bottom of the U.

4. The dental appliance of claim 1 wherein said appliance has a plurality of through holes for receiving wire such that the splint is attchable by wiring to the mandible.

5. The dental appliance of claim 1 wherein said appliance has a plurality of inner and outer slots for receiving wire such that the splint is attachable by wiring to the mandible.

6. The dental appliance of claim 1 wherein the said appliance is indirectly attachable to the mandible by affixing it to arch bars secured to the teeth.

7. The dental appliance of claim 1 wherein the said appliance is indirectly attachable to the mandible by affixing it to brackets secured to the mandible.

8. The dental appliance of claim 1 wherein said splint is made of a material selected from the group consisting of metals, metal alloys, plastics, composite, ceramics, and mixtures thereof.

9. The dental appliance of claim 8 wherein said splint is made of methlymethacrylate.

10. The dental appliance of claim 8 wherein said splint is made of a metal alloy.

11. A method for stabilizing a mandibular fracture comprising the steps of:

placing a splint, having a curvature substantially conforming to the curvature of an 8 inch diameter sphere on the teeth or gingiva of the lower jaw; and fixing the splint to the mandible of the patient.

12. The method of claim 11 wherein the splint is placed in a location superior to the mandible, abutting the teeth on the lower aspect of the splint.

13. The method claim 11 wherein the splint is placed in a location superior to the mandible, abutting the gingiva in the edentulous patient.

14. The method of claim 11 wherein said fixing step consists of wiring the splint to the mandible.

15. The method of claim 11 wherein said fixing step consists of wiring the splint to arch bars affixed to the teeth.

16. The method of claim 11 wherein said fixing step consists of wiring the splint to brackets affixed to the mandible.

17. The method of claim 11 further including the step of screwing fractures into position on the mandible according to the alignment provided by the curvature of the attached splint.

18. The method of claim 11 wherein said splint is placed on the gingiva of a lower jaw and affixed to the mandible.

19. A dental appliance for aligning and stabilizing the mandible for the correction of mandibular fractures comprising a splint having a curvature which substantially conforms to the three dimensional curvature consistent with the Curve of Spee, having an inner border and an outer border, and attachable directly or indirectly to the mandible.

20. A dental appliance for aligning and stabilizing the mandible for the correction of mandibular fractures comprising a splint having a curvature which substantially conforms to the three dimensional curvature consistent with the Curve of Wilson, having an inner border and an outer border, and attachable directly or indirectly to the mandible.

21. A dental appliance for aligning and stabilizing the mandible for the correction of mandibular fractures comprising:

a splint shaped to substantially conform in three dimensions to the curvature of an eight inch diameter sphere, having an inner border and an outer border, and attachable to the mandible.

22. A method for stabilizing a mandibular fracture comprising the steps of:

placing a splint having a curvature substantially conforming to the curvature of an eight inch diameter sphere on the teeth of the lower jaw; and fixing the splint to the mandible of the patient.

23. The method of claim 22 wherein said fixing step is accomplished by wiring the splint to the mandible.

24. The method of claim 22 further including the step of screwing fractures into position on the mandible according to the alignment provided by the curvature of the attached splint.

25. The method of claim 22 wherein said splint is placed on the gingiva of the lower jaw and affixed to the mandible.

* * * * *

UNITED STATES PATENT AND TRADEMARK OFFICE
CERTIFICATE OF CORRECTION

PATENT NO. : 6,227,861
DATED : May 8, 2001
INVENTOR(S) : Cartledge, Richard G. et al.

It is certified that error appears in the above-identified patent and that said Letters Patent is hereby corrected as shown below:

Column 1,
Lines 21 and 25, change "it's" to -- its --.
Line 41, change "realignient" to -- realignment --.

Column 3,
Line 53, after "for" delete -- the --.

Column 4,
Lines 15, 19 and 22, after "invention" insert -- is --.
Line 55, change "it's" to -- its --.

Column 5,
Line 42, after "end 25" insert a -- . --.

Column 6,
Line 1, change "patent's to -- patient's --.
Line 5, after "thereof" insert a -- . --.
Line 26, change "flimly afix" to -- firmly affix --.
Lines 27 and 28, after "outer" change "boarder" to -- border --.
Line 27 after "inner" change "boarder" to -- border --.

Column 7,
Line 5, change "symphyseal/para symphyseal" to -- symphyseal/parasymphyseal --.
Line 28, change "ma-idngs" to -- markings --.

Signed and Sealed this

Eleventh Day of December, 2001

*Attest:*

NICHOLAS P. GODICI
*Attesting Officer*     *Acting Director of the United States Patent and Trademark Office*